United States Patent [19]

Myers et al.

[11] Patent Number: 4,858,767
[45] Date of Patent: Aug. 22, 1989

[54] PLASTIC CONTAINER INSPECTION PROCESS

[75] Inventors: Michael J. Myers, Lawrenceville, Ga.; Warren J. Harwick, Milwaukee, Wis.

[73] Assignee: The Coca-Cola Company, Atlanta, Ga.

[21] Appl. No.: 92,003

[22] Filed: Sep. 2, 1987

[51] Int. Cl.[4] .................. B07C 5/34; G01N 21/90; G01N 35/04
[52] U.S. Cl. ............................ 209/3.1; 73/23; 73/863.92; 209/523
[58] Field of Search ............... 209/3.1, 509, 522–524, 209/552, 555–556, 558, 576, 651–654, 644; 73/23, 24, 863.91, 863.92; 250/372, 373; 15/304

[56] References Cited

U.S. PATENT DOCUMENTS

| 2,255,615 | 9/1941 | Frankel | 15/304 |
| 2,901,625 | 8/1959 | Friedman et al. | 250/372 X |
| 3,266,292 | 8/1966 | Bailey | 73/23 |
| 3,321,954 | 5/1967 | Bailey | 73/23 |
| 3,489,523 | 1/1970 | Clardy et al. | 73/23 U X |
| 3,490,267 | 1/1970 | Gordon | 73/23 |
| 3,516,108 | 6/1970 | Loeffler | 15/304 |

Primary Examiner—Robert B. Reeves
Assistant Examiner—Edward M. Wacyra
Attorney, Agent, or Firm—Eduardo M. Carreras

[57] ABSTRACT

A container inspection process and apparatus is provided for detecting the presence of contaminants present on or absorbed into the walls of plastic containers. The process flushes volatiles from within the container by injecting gas, draws a vapor sample from within the container and analyzes the sample with an ionization instrument.

7 Claims, 2 Drawing Sheets

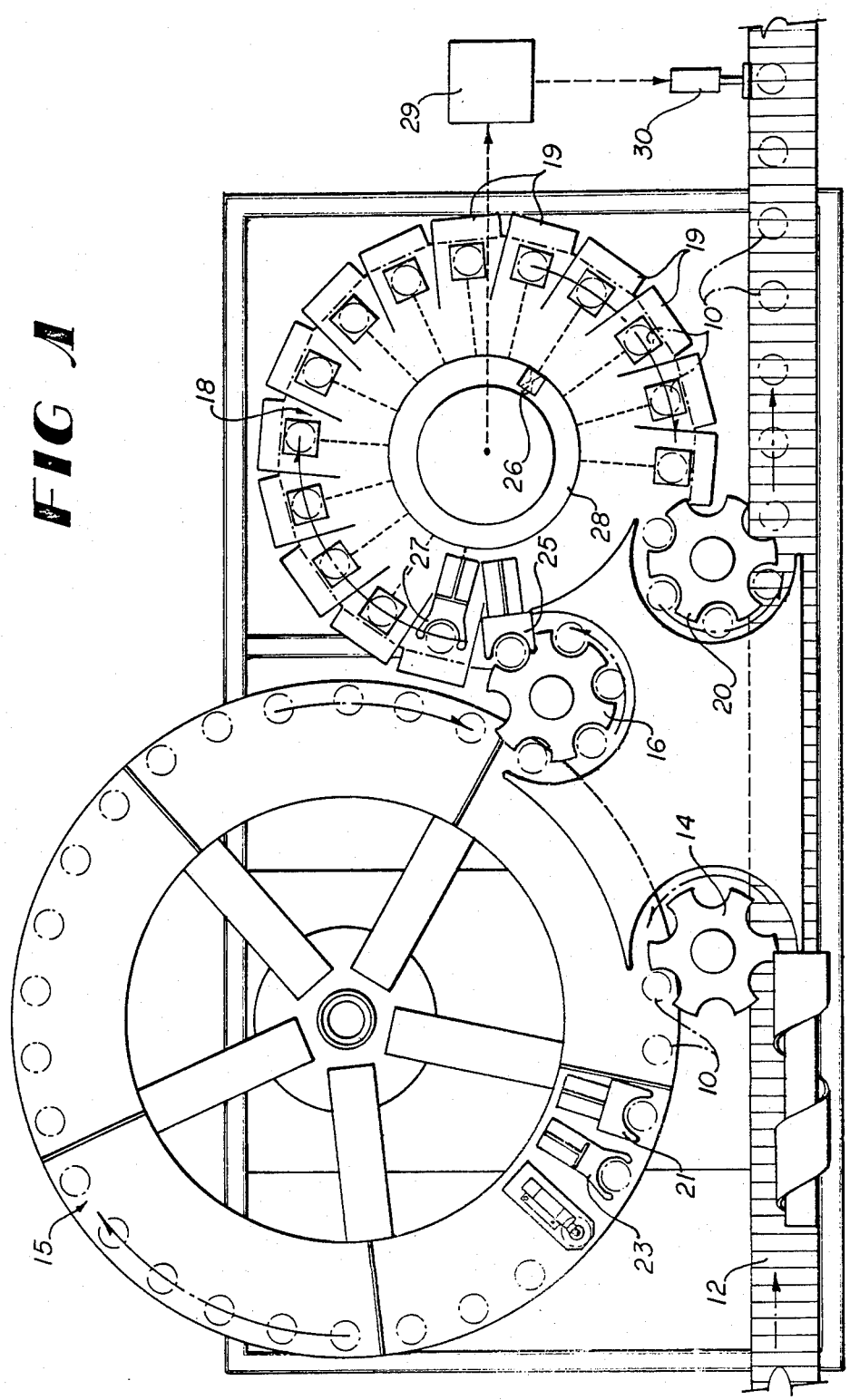

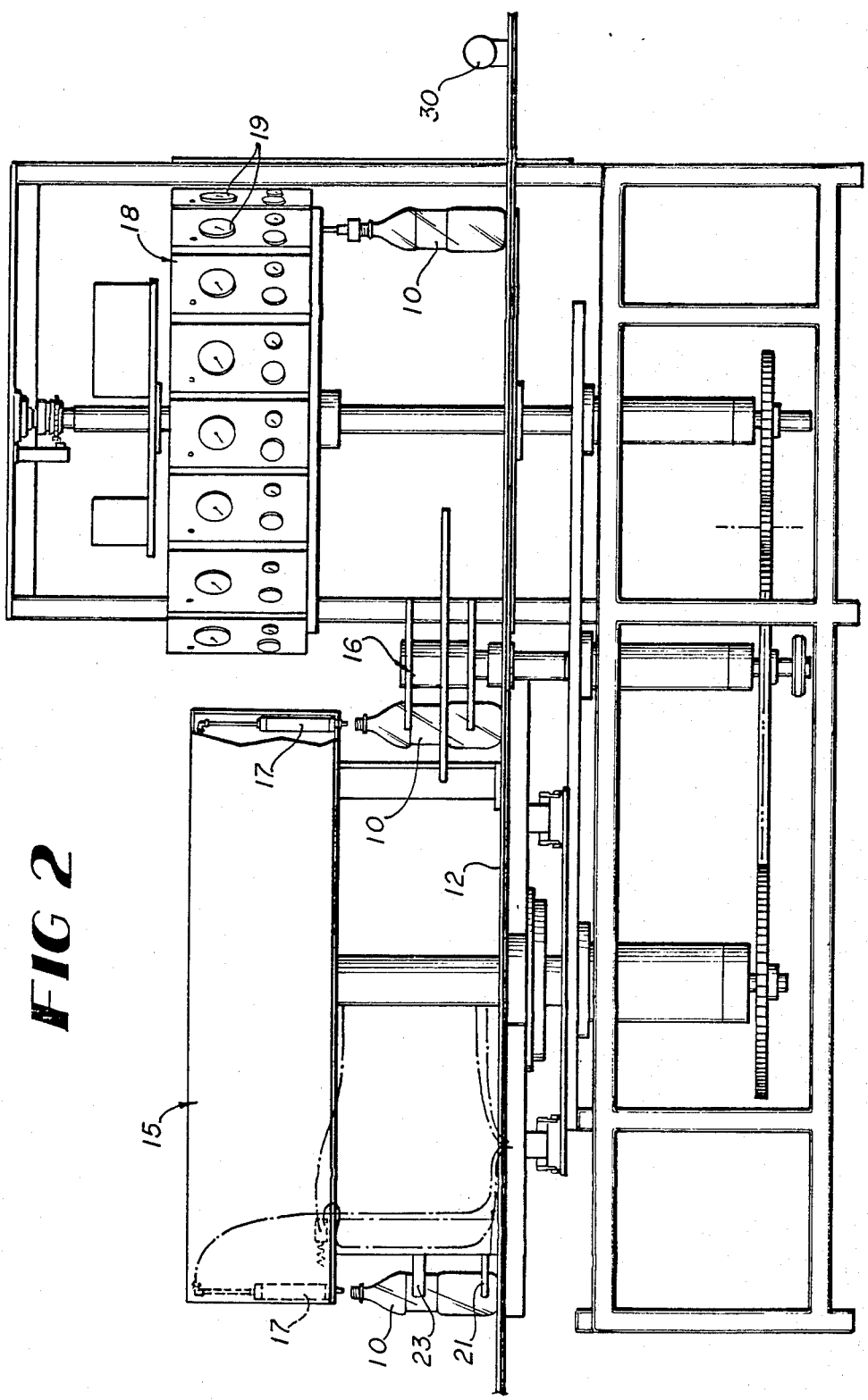

PLASTIC CONTAINER INSPECTION PROCESS

BACKGROUND OF THE INVENTION

1. Field of the Invention

This invention relates to a container inspection process for detecting the presence of contaminants in plastic containers. More specifically, this invention relates to identifying plastic containers which have organic compounds present on or absorbed into the walls of such containers by analyzing the vapors therein.

2. Description of the Prior Art

Plastic containers, such as polyethylene terephthalate (PET) bottles, have long been used for the packaging of carbonated and noncarbonated beverages. Typically, these containers are only used once and then discarded. However, in certain geographic areas, such as central Europe, multiple use containers dominate the beverage container industry. In such areas, the opportunity to use plastic containers is primarily for multiple use containers.

While plastic containers have perceived advantages over glass containers, such as weight and convenience, a perceived disadvantage of reusing plastic containers has been the potential for absorption of certain contaminants into the container walls after the rare occurrence of container misuse by a consumer. These absorbed contaminants have the potential to be desorbed back into the beverage when the container is refilled. Thus, the present process provides a means of identifying certain contaminants that are present on the container walls or that have been absorbed into the container walls.

Generally, conventional container inspection systems were developed for glass containers and were not concerned with absorption of contaminants into the container walls. These conventional systems are typically used for detecting the presence of solid particles or for the detection of contaminants in product-filled containers. For example, see U.S. Pat. No. 4,376,951 to Miyazawa, U.S. Pat. No. 4,551,627 to Wriech, U.S. Pat. No. 4,221,961 to Peyton, U.S. Pat. No. 4,087,184 to Knapp et al., U.S. Pat. No. 4,083,691 to McCormack et al, U.S. Pat. No. 3,966,332 to Knapp et al, and U.S. Pat. No. 4,459,023 to Wriech et al.

However, the present invention provides a novel process for detecting contaminants which are present on or have been absorbed into the walls of plastic containers. Moreover, this invention provides a process which is commercially viable for inspecting and reusing plastic containers in the beverage industry.

SUMMARY OF THE INVENTION

The present invention provides a process for detecting organic contaminants which are present on or absorbed into the walls of plastic containers comprising;
(a) injecting a substantially inert gas into the container to remove the vapors from therein,
(b) drawing a vapor sample from within the container,
(c) analyzing the sample by ionization techniques to detect the presence of contaminants in the container.

Also provides is an apparatus for practicing the process of the present invention.

BRIEF DESCRIPTION OF THE DRAWINGS

One embodiment of the present invention is more fully understood with reference to the following illustration wherein:

FIG. 1 is a top view showing a preferred method for practicing the process of the present invention.

FIG. 2 is a side view of FIG. 1.

DETAILED DESCRIPTION OF THE INVENTION

The process of the present invention employs the surprising discovery that the persistence of organic contaminant volatility as compared to the beverage residue volatility provides a technique for the detection of contaminants presence in reusable plastic containers and particularly plastic bottles. In other words, it has been discovered that the volatiles derived from the beverage residue are not released at the same rate or to the same extent as the volatiles derived from the residue of organic contaminants. When all of the initial volatiles have been removed from the container, the volatiles from the contaminant residue are again released or released more rapidly and are therefore detectable from and distinguished from the volatiles derived from the beverage residue. Thus, this discovery can be employed to discriminate between the volatiles derived from the organic contaminants from the volatiles derived from the beverage residue and hence, the detection of organic contaminants present in the walls of plastic containers.

According to the present process, empty plastic containers which have been returned after use are inspected for contamination by (a) removing all volatiles from within the container by injecting a substantially inert gas into the container, (b) drawing a sample of the newly formed vapors from within the container and (c) analyzing the sample by ionization means to determine the total ionizables present. It is preferred that the present process be employed prior to washing the containers.

Plastic containers as used herein include containers made from any suitable polymer, copolymer or resins useful for food contact applications. Examples of such materials include but are not limited to PET, polyvinyl chloride, and polycarbonate.

The gas employed herein can be injected into the container using any of the well known techniques for accomplishing such an objective. For example, any suitable gas injection tube or nozzle can be inserted into the container from the opened dispensing end or neck. The nozzle should leave a space or outlet for the volatiles from within the container to be vented into the atmosphere. Typically, the nozzle is a cylindrical tube having an inside diameter corresponding to about 10% to about 80% of the inside diameter of the mouth of the container. Generally, the nozzle will be inserted into the container to a point from about 0.5 to about 7.0 inches (about 1.25 cm to about 18.0 cm) from the top of the container depending on the container size. It is preferred to use multiple injections of the gas to more completely remove the volatiles from the container. Accordingly, it is preferred to use from two to seven gas injections with five injections being most preferred when air is used as the injection gas.

The gas used in accordance with this invention can be any substantially inert gas that will not adversely affect the contaminant detection means by providing false readings. Suitable gases include nitrogen, helium, argon, carbon dioxide, air and the like. Preferably, air whichis substantially free from contaminants is used because of its lower cost.

The duration, temperature and pressure employed for the gas injection depends on the particular gas utilized. For example, it is preferred that the duration of each gas injection be from about 0.1 to about 10 seconds, preferably from about 0.5 to about 1.5 seconds, and most preferably, when using air, for about 1 second. The pressure may vary from about 20 psig (about 1.4 kg/sq. cm. gage) to about 60 psig (about 4.0 kg/sq. cm. gage) and preferably is about 40 psig (about 3.0 kg/sq. cm. gage) when using air. The gas temperature can vary from about 10° C. to about 50° C., but it is preferably ambient (about 20° C.). The linear velocity is established by the pressure ratio to obtain critical flow. Typically, the linear velocity is between about 900 and about 1300 feet per second with about 1100 feet per second (sonic) being preferred. The gas displacement volume is generally form about 50% to about 150% of the volume capacity of the container.

Once the volatiles are removed from the containers, samples of the newly formed vapors are drawn. Generally, the samples can be drawn utilizing conventional pumps, venturi devices or blowers with or without a vacuum accumulator or vacuum cylinder. It is preferred to seal the container when drawing the sample in order to ensure that no contaminants from the atmosphere will enter the ignition chamber of the ionization instrument. Partial sealing is possible if the surrounding air is substantially free of airborne contaminants.

The vapor samples drawn from the containers are preferably analyzed by ionization techniques to identify the total ionizables present (TIP). A TIP reading, which is in excess of the established TIP reading for uncontaminated containers indicates organic contaminants have been placed in the container. A standard TIP reading can be determined by simply testing an uncontaminated container in the environment in which the process is to be used.

Such ionization techniques include flame ionization (including laser-enhanced flame ionization) and photoionization with the photoionization including ultraviolet photoionization. It is preferred to use ultraviolet (UV) photoionization wherein the vapor samples are passed over a ultraviolet lamp. Such photoionization techniques, including ultraviolet photoionization techniques are known in the art. One advantage to using ionization techniques is that it has been found that the ionization of the vapor sample produces an electric current flow that is proportional to the amount of contamination. Thus, ionization allows for a quantitative reading of TIP.

While ionization techniques are the preferred mode for analyzing the presence of contaminants herein, contemplated equivalent analytical techniques include the various mass spectrometry techniques which separate and identify ions by their mass. Such mass spectrometry techniques are believed to be capable of application in the present invention and are included herein.

The present invention is directed to detecting contaminants which are generally undetected by observation. Typically, these contaminants are organic compounds found in chemical mixtures available to consumers such as in cleaning agents, gasoline, motor oil, kerosene, paint thinner or the like which have been placed into the container by the consumer for storage or other purposes.

The detectable compounds of this invention cover a wide range of organic compounds and include chemical mixtures containing one or more of these compounds. Typically, these organic compounds are used as solvents in commercial chemical mixtures but are not limited to such uses.

Preferably, the present process can be employed to detect hydrocarbons, alcohols, ketones or mixtures containing one or more of these compounds. Specifically included are chemical mixtures wherein the hydrocarbons, alcohols or ketones are present from trace amounts to 100% by volume. The present process is most preferably used to detect hydrocarbons.

Examples of such hydrocarbons include alkanes, alkenes, alkadienes, acetylenes, acyclic terpenes, cycloparaffins, cycloolefins, cycloacetylenes, aromatics, and cyclic terpenes. Preferred hydrocarbons are alkanes, alkenes, aromatics and cyclic terpenes and most preferred are petroleum derived hydrocarbons.

Examples of alcohols detectable by the present process include monohydric alcohols; aliphatic, alicyclic, and aromatic; dihydric; trihydric; and polyhydric alcohols. The present process is preferably employed to direct alicyclic and aromatic alcohols.

The ketones detectable by the present process include all compounds having at least one carbonyl group and includes monoketones, polyketones and hycrocyclic ketones.

While the above lists have been included as way of example, it is believed that the present invention will detect all organic compounds or mixtures containing such compounds which may be present on or absorbed in the container walls. Thus, the above provided lists of compounds should not be used to limit the scope of this invention which shall include all organic compounds which are within the analytical capabilities of the detection equipment.

The contaminants which can be detected using the preferred photoionization analysis are organic compounds having an ionization potential of below about 11.2 eV or below about 10.6 eV depending on the light source employed in the photoionization instrument. This includes compounds having multiple components wherein at least one of the hydrocarbons or other organic compounds present have an ionization potential of below about 11.2 eV or about 10.6 eV. While light sources with the ability to ionize compounds having an ionization potential of 11.2 eV can be employed, those with an ionization potential of 10.6 eV are commercially preferred because of their durability and decreased maintenance requirements.

In a preferred embodiment of this invention as illustrated in FIG. 1, an in-line testing system is provided which can detect organic contaminants which have been placed in plastic containers. Referring to FIGS. 1 and 2, used plastic containers 10 are placed into an existing bottling line conveyor 12. The containers 10 are removed from conveyor 12 by a first transferring means 14 which accepts the containers 10 from the conveyor 12 and transfers them to a first rotary disc 15. Rotary disc 15 has multiple nozzles 17 for injecting a substantially inert gas into the containers 10. The first rotary disc 15 has cradles 21 for aligning the containers 10 and grippers 23 for holding the containers 10 in place during the gas injections. The nozzles 17 are attached to a source of compressed gas and are positioned above each cradle 21 and inserted into the containers 10. The containers 10 are rotated around the disc 15 while receiving one or more injections of the gas employed by nozzles 17.

After the gas injection, the containers 10 are then transferred to a second rotary disc 18 by a second transferring means 16. The second rotary disc 18 has cradles 25 and grippers 27 at each station. Each station is connected to a vacuum accumulator 28 which is activated by a venturi 26. A vapor sample from each container 10 as the containers 10 are rotated around the second rotary disc 18. The vapor sample is transported to a UV photoionization instrument 19 which is positioned above each cradle 25. The UV photoionization instruments 19 analyze the vapor samples for the presence of total ionizables present in a conventional manner.

Preferably, the UV photoionization instruments 19 are connected to a microprocessor 29 which receives an electronic signal from the instruments 19 and sends an electronic signal to a rejection means 30. The microprocessor 29 receives the electronic signal representing the numerical reading from the photoionization instrument 19 for a particular container 10 and compares it against a predetermined value. If the reading is above or below the predetermined value, the microprocessor 29 sends a signal to the rejection means 30 to reject the container 10.

The containers 10 are transferred by a third transferring means 20 to the conveyor 12 after testing. The contaminated containers are then rejected by the rejecting means 22 which is typically an air blast or air ram which physically removes the container 10 from the conveyor 12 as known in the art.

The transferring means 14, 16 and 20 are typically star wheels which are timed in sequence to systematically communicate with the rotary discs 15 and 18 and with the conveyor 12 and operate continuously. Such star wheels utilize known principles of operation and are currently used in the beverage industry.

SPECIFIC EMBODIMENTS

Test Procedure #1

In order to test for the contaminants by the present invention, multiple 1.5 liter PET bottles were prepared according to the following procedure. Each bottle was filled with orange soda sold under the trademark "Minute Made" (a product of The Coca-Cola Company), capped, and stored for 24 hours. This beverage was used because preliminary tests indicated that it had the highest total ionizables present of the broad range of carbonated beverages tested thereby making it the most severe case. The bottles were then opened and the beverage was removed. The empty bottles were again capped and stored for one hour, seven days and fourteen days respectively. After storage, each bottle was uncapped and tested before injecting air by drawing a vapor sample and analyzing the sample with a UV photoionization instrument. The bottles were then treated by injecting five separate injections of a duration of one second of ambient air into each bottle at 40 psig, drawing a vapor sample, and analyzing the samples with a UV photoionization instruments. The photoionization instruments were commercially purchased from Photovac, Inc. The UV photoionization instrument had a continuous voltage source of 12.0 Vdc with ±0.2 output and was frequently calibrated against a 100 ppm isobutylene (in air) standard gas. The UV lamp crystal in the UV photoionization instrument was cleaned frequently and the inlet filters were changed on daily basis. The instrument reading indicates total ionizables present (TIP) by reference to the isobutylene. Representative results are shown in Table I.

Test Procedure #2

The second test procedure was similar to test procedure #1 except that after a 24 hour storage of the beverage, various contaminants were placed into the empty containers. The contaminants were left in the containers for 14 days, emptied, and stored with closures. Ionization readings were taken at various time intervals. Representative results are shown in Table II (see "with closures").

Test Procedure #3

The third test procedure was identical to test procedure #2 except that the beverage was not placed into the containers and that the containers were stored without closures prior to the testing. The results are shown in Table III (see "without closures").

Results

The results as shown in Table I, II and III indicate that contaminants having an ionization potential below about 10.6 eV (the limitations of the UV light source) can be reproducible detected in reused plastic containers using the process of the present invention. In each test, the beverage residue volatiles did not affect the contaminant reading even though the beverage, residue containers had a high TIP reading when tested alone. As shown in Table I, the volatiles of the beverage residue can be totally removed using the gas injection pretreatment. However, as shown in Tables II and III, the volatiles from the contaminant residue continue to appear and give high TIP reading even after the gas pretreatment.

Not intending to be bound to theory, it is believed that the pretreatment described in this invention, removes the volatiles associated with the beverage residue due to the air turbulence or scrubbing action from the gas injection pretreatment. The elimination or reduction of volatility of any remaining beverage residue after pretreatment with gas injections greatly reduces or eliminates the possibility of registering a TIP reading that would result in the rejection of the container as containing contaminant. The volatility of the organic contaminants persist after the gas injections and those contaminants that are present on or absorbed in the plastic container walls are detected as evidenced by the TIP reading as compared to the standard TIP reading for a clear container.

It is to be understood that the present invention is not to be limited by the drawings or the embodiments set forth herein which have been provided merely to demonstrate operability. Modifications, variations and equivalent embodiments can be employed without departing from the spirit and scope of this invention.

TABLE I

| DETECTION FOR TOTAL IONIZABLES PRESENT (TIP) FROM BEVERAGE RESIDUE* | | | |
|---|---|---|---|
| STORAGE TIME | NO. OF SAMPLES | TIP READING RANGE | |
| | | BEFORE | AFTER |
| 1 hour | 21 | 98 to 141 | −3 to −8 |
| 7 days | 21 | 5 to 15 | −1 to −3 |

TABLE I-continued

DETECTION FOR TOTAL IONIZABLES PRESENT (TIP) FROM BEVERAGE RESIDUE*

| STORAGE TIME | NO. OF SAMPLES | TIP READING RANGE BEFORE | AFTER |
|---|---|---|---|
| 14 days | 20 | 2 to 19 | −4 to −5 |

*All tests used orange soda sold under the Trademark "MINUTE MAID" (a registered trademark of The Coca-Cola Company) using 5 air injections of 1 second duration at 40 psig.

TABLE II

DETECTION FOR TOTAL IONIZABLES PRESENT (TIP) FROM CONTAMINANT RESIDUE

| CONTAMINANT | CONCENTRATION | DAYS STORED | TIP READINGS WITH CLOSURES |
|---|---|---|---|
| Acetone | 100% | 1 | 2000 |
|  |  | 10 | 2000 |
|  |  | 25 | 2000 |
| Gasoline | 100% | 1 | 2000 |
|  |  | 10 | 1600 |
|  |  | 25 | 1000 |
| Diesel Fuel | 100% | 1 | 2000 |
|  |  | 10 | 2000 |
|  |  | 25 | 1030 |
| Kerosene | 100% | 1 | 2000 |
|  |  | 10 | 2000 |
|  |  | 25 | 1390 |
| Isopropanol | 100% | 1 | 420 |
|  |  | 10 | 600 |
|  |  | 25 | 270 |
| Motor Oil (clean) | 100% | 1 | 90 |
|  |  | 10 | 90 |
|  |  | 25 | 20 |

TABLE III

DETECTION FOR TOTAL IONIZABLES PRESENT (TIP) FROM CONTAMINANT RESIDUE

| CONTAMINANT | CONCENTRATION | DAYS STORED | TIP READINGS WITHOUT CLOSURES |
|---|---|---|---|
| Acetone | 100% | 1 | 767 |
|  |  | 3 | 27 |
|  |  | 7 | 10 |
| Diesel Fuel | 100% | 1 | 114 |
|  |  | 3 | 89 |
|  |  | 7 | 86 |
| Gasoline | 100% | 1 | 532 |
|  |  | 3 | 269 |
|  |  | 7 | 94 |
| Isopropanol | 100% | 1 | 201 |
|  |  | 3 | 192 |
|  |  | 7 | 182 |
| Kerosene | 100% | 1 | 836 |
|  |  | 7 | 271 |
| Motor Oil (used) (trace gasoline) | 100% | 1 | 341 |
|  |  | 3 | 129 |
|  |  | 7 | 86 |

What is claimed is:

1. A continuous process for detecting organic contaminants present on or absorbed into the walls of plastic containers comprising:
   placing said containers on a first rotary disc,
   injecting a substantially inert gas into said containers as the containers are rotating around said first rotary disc,
   transferring said containers from said first rotary disc to a second rotary disc having (a) multiple vacuum means for drawing samples of newly formed vapors from within said containers and (b) multiple ionization means for analyzing said samples,
   drawing said samples from said containers, analyzing said samples for total ionizables present as said containers are rotating around said second rotary disc,
   removing said containers from said second rotary disc, and
   rejecting said containers in which said total ionizables present are above or below a predetermined value.

2. The process of claim 1 wherein said containers are first placed on a conveyor and are placed on said first rotary disc by means of a first star wheel.

3. The process of claim 2 wherein said containers are transferred from said first rotary disc to said second rotary disc by means of a second star wheel.

4. The process of claim 3 wherein said containers are removed from said second rotary disc by means of a third star wheel.

5. The process of claim 4 wherein said first, second, and third star wheels and said first and second rotary disc are timed in sequence to systematically communicate continuously.

6. The process of claim 1 wherein said ionization means electrically communicates with a microprocessor capable of accepting a first electric signal from said ionization means, comparing said first electric signal to a predetermined valve, and sending a second electric signal to a rejection means when said first electrical signal is greater than said predetermined valve.

7. An apparatus for continually detecting organic contaminants present on or absorbed into the walls of plastic containers moving on a beverage filling conveyor system comprising:
   first means for removing said containers from said beverage filling conveyor system and feeding said containers to a first rotary disc, said first rotary disc having multiple injection means for injecting a substantially inert gas into said containers as said containers are rotating around said first rotary disc,
   second means for removing said containers from said first rotary disc and feeding said containers to a second rotary disc, said second rotary disc having (a) multiple vacuum means for drawing samples of newly formed vapors from within said containers and (b) multiple ionization means for analyzing said samples,
   third means for removing said containers from said second rotary disc and feeding said containers onto said beverage filling conveyor system, and
   rejecting means for rejecting said containers where the total ionizables present as measured by said ionization means are above or below a predetermined value.

* * * * *